United States Patent [19]

Ogawa et al.

[11] Patent Number: 5,308,875
[45] Date of Patent: May 3, 1994

[54] THERAPEUTIC COOLANT FOR THE LOCAL TREATMENT OF BURN

[75] Inventors: Yutaka Ogawa, Kyoto; Hideaki Doi, Yao, both of Japan

[73] Assignee: Nippon Petrochemicals Co., Ltd., Tokyo, Japan

[21] Appl. No.: 52,812

[22] Filed: Apr. 28, 1993

Related U.S. Application Data

[63] Continuation of Ser. No. 697,188, May 8, 1991, abandoned.

[30] Foreign Application Priority Data

May 8, 1990 [JP] Japan ................................ 2-118069

[51] Int. Cl.⁵ ............................................ A61K 31/01
[52] U.S. Cl. ............................ 514/762; 424/DIG. 13
[58] Field of Search ................ 514/762; 424/DIG. 13

[56] References Cited

U.S. PATENT DOCUMENTS 4,454,159  6/1984  Musher ................................ 514/21
4,849,211  7/1989  Schrauzer ............................ 424/45

OTHER PUBLICATIONS

Chemical Abstracts, vo. 89, 1978, p. 64, Abstract No. 89:157618t.
Chemcial Abstracts 89:157618t (I), 1978.
Chemical Abstracts 107:28412n (II), 1987.
Balsam et al.-Cosmetics, Science & Technology 2nd ed. vol. 1 pp. 40,188,189 (1972).

Primary Examiner—Frederick E. Waddell
Assistant Examiner—K. Weddington
Attorney, Agent, or Firm—Scully, Scott, Murphy & Presser

[57] ABSTRACT

A therapeutic coolant for the local treatment of burn is provided wherein said coolant consisting of squalene, squalane, or mixtures thereof.

A method of treating burn is provided wherein said method comprising :
applying a therapeutic coolant cooled to a temperature range from −10 to −60° C., said coolant selected from the group consisting essentially of squalene, squalane, or mixtures thereof.

2 Claims, No Drawings

THERAPEUTIC COOLANT FOR THE LOCAL TREATMENT OF BURN

This is a continuation of copending application(s) Ser. No. 697,188 filed on May 8, 1991, which is now abandoned.

BACKGROUND OF THE INVENTION (1) Field of the Invention

The present invention relates to a therapeutic coolant for the local treatment of burn, specifically in its early stages.

(2) Description of the Prior Art

It has been well known that cooling by tap water is effective for the treatment of burn in its early stages. Although it is a convenient method, it is necessary to sterilize the water in advance for the purpose of preventing infection. Tap water itself does not have an intrinsic therapeutic effect for burn. Therefore, a further medical treatment such as application of an ointment to the burned skin is necessary for remedy after cooling the region by tap water.

One of the principal advantages of water such as tap water as a coolant is that appropriate latent heat accompanying the change in state of water such as vaporization can be utilized in cooling. In other materials wherein such latent heat can not be utilized, it is inevitable to cool them to an extremely low temperature sufficient to make them exhibit their cooling effect. However, it is sometimes difficult to cool to such a low temperature, and there is a fear of suffering from frostbite. Conventional oily medicines, for example, applied to the skin have not a sufficient cooling effect, because they have a tendency to become a solid when cooled to such an extremely low temperature. As for local protection medicines for the skin such as glycerine, mel, vaseline and the like, they have not such a tendency to be solidified but become too viscous to be applied smoothly to the skin at an extremely low temperature, and they also have not also a sufficient cooling effect.

For the above reasons, there is a desire for a more efficient and convenient coolant to be used for remedy of burn in its early stages.

SUMMARY OF THE INVENTION

It is an object of the present invention to provide a convenient, therapeutic coolant for the local treatment of burn.

DETAILED DESCRIPTION OF THE INVENTION

The first aspect of the present invention is directed to a therapeutic coolant for the local treatment of burn wherein said coolant comprises squalene, squalane, or mixtures thereof.

The second aspect of the present invention is directed to a method of treating burn by applying a therapeutic coolant cooled to a temperature range from $-10$ to $-60°$ C., said coolant being selected from the group consisting essentially of squalene, squalane, and mixtures thereof.

In the present invention, squalene, squalane, or mixtures thereof is cooled to an extremely low temperature such as $-10$ to $-60°$ C., preferably $-20$ to $-50°$ C., more preferably $-40°$ C., and the resultant coolant is used as a therapeutic coolant for the treatment of burn its early stages. At a temperature of more than $-10°$ C., the cooling effect is insufficient.

Although squalene, squalane, or mixtures thereof maintains its liquid state at a temperature not more than $-60°$ C., it is not practical to cool it to such an extremely low temperature, but also not safe because there is a fear of suffering from frostbite.

Squalene, squalane, or mixtures thereof has a melting point sufficiently low to be able to maintain its liquid state and can form a low viscous liquid even at a temperature range from $-10$ to $-60°$ C.

Further, a coolant comprising squalene, squalane, or mixtures thereof cooled to the temperature range aforesaid is sterilized in the course of said cooling, and there is almost no fear of infection.

In the present invention, squalene or squalane may be a natural product or a synthetic product, said natural product being squalene or squalane extracted from animal oil or vegetable oil such as shark liver oil or olive oil. Squalane obtained by hydrogenation of the carbon to carbon unsaturated double bonds in squalene may be used. Further, mixtures of squalene and squalane in any weight ratio may be employed in the present invention. Among them, squalane is most preferable, because of its excellent oxidation stability.

Squalene, squalane, or mixtures thereof has not any sensitization, and may be applied directly to the local burned skin to achieve the objective immediately after burn.

Squalene, squalane, or mixtures thereof may be in an amount of 0.001 to 1 g./cm$^2$ for burned skin region, but it is not necessarily limited to such a range.

Squalene, squalane, or mixtures thereof of the present invention may be blended with other known therapeutic stuffs used for the local treatment of the skin and mucosa. Examples of the therapeutic stuff include conventional local astringents; conventional local protective medicine such as white vaseline; antiphlogistic-analgesics; disinfectants such as iod povidone, gluconic acid chlorhexydine; antibacterial drugs such as silver sulfadiazine, gentamicin sulfuric acid; antihistaminics; steroid and non-steroid antiinflammatory drugs such as betamethasone valeric acid; enzyme type antiphlogistics; immunosuppressants; antiinflammatory drugs such as guaiazulene; and the like.

Antioxidants such as vitamin E may be also employed to improve the oxidation stability of squalene.

Diluents such as hydrocarbons which has no stimulus to skins, may be also blended with the coolant of the present invention.

EXPERIMENT

Although the present invention has been described in conjunction with preferred embodiments, it is to be understood that modification and variations may be resorted to without departing from the spirit and scope of the invention, as those skilled in the art will readily understand.

Experimental Method

Male Wistar rats (weighing 32.6 to 32.7 pounds) were used in the following experiments. After removing the hair from the back of each rat by means of a depilatory lotion, the bared back skin was applied with hot water to produce deep dermal burn extending over the area having a diameter of 28 mm on either side of the back. The burned skin on the right side is referred to as the treated side, and that on the left side as the control side.

Sixty rats were used to form 3 groups of 20 each. The backs of the rats in each group were burned in the manner mentioned above, and treated as follows. A specimen was collected from each of the wound after 24 hours and 1 week. Pathological specimens were prepared by means of the hematoxylin and eosin stain and inspected under an optical microscope.

1st Group

Right side Squalene cooled to −40° C. in advance was applied 5 times to the wound in an amount of 0.1 g/a time at 10 seconds intervals.

Left side : control (untreated)

2nd Group :

Right side : The same procedure as above was performed with squalane (at −40° C.)

Left side : control (untreated) 3rd Group :

Right side : The same procedure as 1st Group was performed with distilled water (at 20° C.).

Left side : control (untreated)

Results

The following observations on the pathological tissue were given after 24 hours and 1 week:

An eosinophilic layer which were supposed to be the changes to a morbid state by heat were observed in the upper dermis over a relatively wide area in the control Groups. Such a destructive changes were mild in the treated groups. The swelling of the collagen fibers and destruction of the adnexa were observed remarkably in the control group. In the deep dermis, bright edematous layer showed up more or less even in the treated group, but they were observed remarkably in the control group. And, the new growth of the capillaries in the dermis observed in the control group.

Table 1 gives the results showing a relatively minor change of the skin in the treated group.

The appraisals in Table 1 were based on the followings :

1—observed all over
2—observed over a majority area
3—observed over a majority of about half the number
4—observed partially
5—scarcely observed

TABLE 1

|  | 1st Group | | 2nd Group | | 3rd Group | |
|---|---|---|---|---|---|---|
|  | treated | untreated | treated | untreated | treated | untreated |
| An eosinophilic layer which are supposed to be the changes to a morbid state by heat | 4 | 1 | 4 | 1 | 2 | 1 |
| The swelling of the collagen fibers and destruction of the adnexa | 4 | 1 | 4 | 1 | 2 | 1 |
| The bright edematous layer in the deep dermis | 4 | 1 | 4 | 1 | 2 | 1 |
| New growth of the capillaries in the dermis | 4 | 1 | 4 | 1 | 1 | 1 |

What is claimed is:

1. A method of treating a burn by applying a therapeutic coolant cooled to a temperature range from −10° C. to −60° C., said coolant comprising squalene, squalane of mixtures thereof in am amount effective to treat a burn when applied to said burn at a temperature range from −10° C. to −60° C.

2. The method according to claim 1 wherein said amount effective to treat a burn is from about 0.001 to 1 g/cm$^2$ per burned skin region.

* * * * *

UNITED STATES PATENT AND TRADEMARK OFFICE
CERTIFICATE OF CORRECTION

PATENT NO. : 5,308,875
DATED : May 3, 1994
INVENTOR(S) : Yutaka Ogawa, et al.

It is certified that error appears in the above-indentified patent and that said Letters Patent is hereby corrected as shown below:

On the title page, Item [56], Under "OTHER PUBLICATIONS", line 3: "Chemcial" should read --Chemical--

Column 2, line 14: "Of" should read --of--

Column 4, line 36, Claim 1: "of" should read --or--

Column 4, line 36, Claim 1: "am" should read --an--

Signed and Sealed this

Third Day of January, 1995

Attest:

BRUCE LEHMAN

Attesting Officer     Commissioner of Patents and Trademarks